United States Patent [19]

Eberlein et al.

[11] 4,134,980
[45] Jan. 16, 1979

[54] PHENYLALKYLAMINO-ALKYL DERIVATIVES OF QUINAZOLINONE AND PHTHALAZINONE

[75] Inventors: Wolfgang Eberlein; Volkhard Austel, both of Biberach; Joachim Heider; Jurgen Dammgen, both of Warthausen; Rudolf Kadatz, Biberach, all of Fed. Rep. of Germany; Christian Lillie; Walter Kobinger, both of Vienna, Austria

[73] Assignee: Boehringer Ingelheim GmbH, Ingelheim am Rhein, Fed. Rep. of Germany

[21] Appl. No.: 827,142

[22] Filed: Aug. 24, 1977

[30] Foreign Application Priority Data

Sep. 1, 1976 [DE] Fed. Rep. of Germany ....... 2639291

[51] Int. Cl.² .................. C07D 237/32; C07D 239/72
[52] U.S. Cl. ............................. 424/250; 424/251; 544/237; 544/287
[58] Field of Search ........ 260/250 P, 251 R, 251 QA, 260/251 QB; 424/250, 251; 544/237, 287

[56] References Cited

U.S. PATENT DOCUMENTS

| | | | |
|---|---|---|---|
| 3,748,327 | 7/1973 | Beyerle et al. | 260/251 QA |
| 3,829,420 | 8/1974 | Inaba et al. | 260/251 QB |
| 3,905,976 | 9/1975 | Hardtmann | 260/251 QA |

Primary Examiner—Nicholas S. Rizzo
Attorney, Agent, or Firm—Hammond & Littell

[57] ABSTRACT

Compounds of the formula

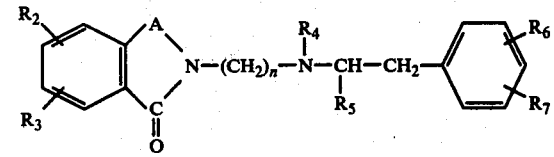

wherein A is

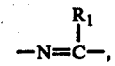

where $R_1$ is hydrogen or alkyl of 1 to 3 carbon atoms;
$R_2$ is alkoxy of 1 to 3 carbon atoms;
$R_3$ is alkoxy of 1 to 3 carbon atoms or, together with $R_2$, methylenedioxy or ethylenedioxy;
$R_4$ is hydrogen, alkyl of 1 to 3 carbon atoms or benzyl;
$R_5$ is hydrogen or alkyl of 1 to 3 carbon atoms;
$R_6$ is hydrogen or alkoxy of 1 to 3 carbon atoms;
$R_7$ is alkoxy of 1 to 3 carbon atoms or, together with $R_6$, methylenedioxy or ethylenedioxy; and
n is 2 or 3;

and non-toxic, pharmacologically acceptable acid addition salts thereof; the compounds as well as their salts are useful as heart rate reducers and mild antihypertensives.

7 Claims, No Drawings

PHENYLALKYLAMINO-ALKYL DERIVATIVES OF QUINAZOLINONE AND PHTHALAZINONE

This invention relates to novel N-(phenylalkylaminoalkyl)-substituted quinazolinones and phthalazinones and nontoxic acid addition salts thereof, as well as to various methods of preparing these compounds.

More particularly, the present invention relates to a novel class of N-substituted quinazolinones and phthalazinones represented by the formula

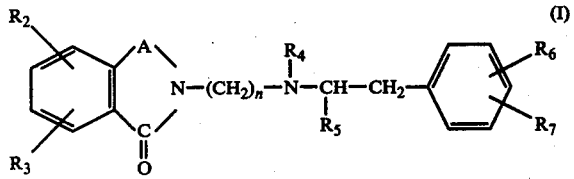

wherein A is

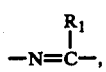

where $R_1$ is hydrogen or alkyl of 1 to 3 carbon atoms;
$R_2$ is alkoxy of 1 to 3 carbon atoms;
$R_3$ is alkoxy of 1 to 3 carbon atoms or, together with $R_2$, methylenedioxy or ethylenedioxy;
$R_4$ is hydrogen, alkyl of 1 to 3 carbon atoms or benzyl;
$R_5$ is hydrogen or alkyl of 1 to 3 carbon atoms;
$R_6$ is hydrogen or alkoxy of 1 to 3 carbon atoms;
$R_7$ is alkoxy of 1 to 3 carbon atoms or, together with $R_6$, methylenedioxy or ethylenedioxy; and
n is 2 or 3;

or a non-toxic, pharmacologically acceptable acid addition salt thereof.

A preferred sub-genus thereunder is constituted by compounds of the formula I where
$R_1$ and $R_5$ are each hydrogen, methyl, ethyl, n-propyl or isopropyl;
$R_4$ is hydrogen, methyl, ethyl, n-propyl, isopropyl or benzyl;
$R_2$, $R_3$ and $R_7$ are each methoxy, ethoxy, n-propoxy or isopropoxy;
$R_6$ is hydrogen, methoxy, ethoxy, n-propoxy or isopropoxy;
$R_2$ and $R_3$, together with each other, are methylenedioxy or ethylenedioxy;
$R_6$ and $R_7$, together with each other, are methylenedioxy or ethylenedioxy; and
n is 2 or 3;

and non-toxic, pharmacologically acceptable acid addition salts thereof.

A further, especially preferred sub-genus thereunder is constituted by compounds of the formula I where
$R_2$ and $R_3$ are methoxy in the 6- and 7-position, respectively, or, together with each other, methylenedioxy or ethylenedioxy;
$R_4$ is hydrogen or methyl;
$R_5$ is hydrogen;
$R_6$ is hydrogen or methoxy in the 3-position;
$R_7$ is methoxy in the 4-position or, together with $R_6$, methylenedioxy or ethylenedioxy; and
n is 2 or 3;

and non-toxic, pharmacologically acceptable acid addition salts thereof.

The compounds embraced by formula I may be prepared by the following methods:

Method A

By reacting a compound of the formula

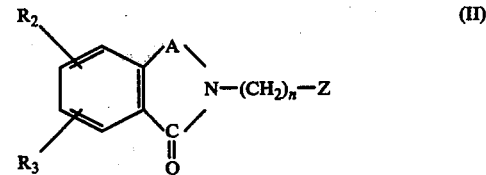

wherein $R_2$, $R_3$, A and n have the same meanings as in formula I, and
Z is a leaving-group, such as chlorine, bromine, iodine, alkylsulfonyloxy or arylsulfonyloxy, with a phenylalkylamine of the formula

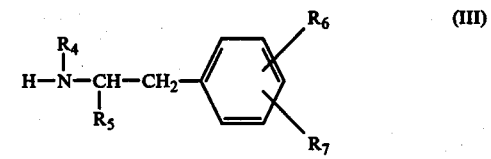

wherein $R_4$, $R_5$, $R_6$ and $R_7$ have the same meanings as in formula I.

The reaction is carried out in an inert solvent, such as ether, tetrahydrofuran, methylformamide, dimethylformamide, dimethylsulfoxide, chlorobenzene or benzene, and depending upon the reactivity of substituent Z, at a temperature between −50 and +250° C, but preferably at the boiling point of the particular solvent which is used. The presence of an acid-binding agent, such as an alkali metal alcoholate, an alkali metal hydroxide, an alkali metal carbonate, especially potassium carbonate, or a tertiary organic base, particularly triethylamine or pyridine, or of a reaction accelerator, such as potassium iodide, is of advantage.

Method B

By reacting a compound of the formula

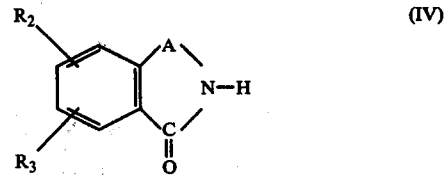

wherein A, $R_2$ and $R_3$ have the same meanings as in formula I, with a phenylalkylamine of the formula

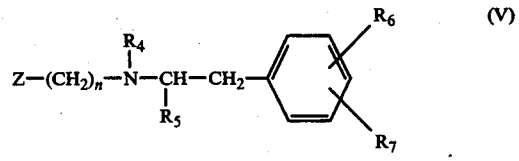

wherein $R_4$, $R_5$, $R_6$ and n have the same meanings as in formula I, and
Z has the same meanings as in formula II.

The reaction is carried out in an inert solvent, such as acetone, dimethylformamide, dimethylsulfoxide or chlorobenzene, and, depending upon the reactivity of substituent Z, at a temperature between 0 and 150° C, but preferably at the boiling point of the particular solvent which is used. The presence of an acid-binding agent, such as an alkali metal alcoholate, an alkali metal hydroxide, an alkali metal carbonate, especially potassium carbonate, an alkali metal amide or a tertiary organic base, particularly triethylamine or pyridine, or of a reaction accelerator, such as potassium iodide, is of advantage.

Method C

By reacting an aldehyde of the formula

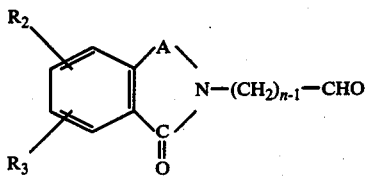

wherein $R_2$, $R_3$, A and n have the same meanings as in formula I, or an acetal thereof, with an amine of the formula III in the presence of catalytically activated hydrogen.

The reductive amination is carried out with hydrogen in the presence of a hydrogenation catalyst, such as palladized charcoal, at a hydrogen pressure of 5 atmospheres, in a solvent, such as methanol, ethanol or dioxane, and at a temperature between 0 and 100° C, but preferably between 20 and 80° C.

Method D

By reacting an amine of the formula

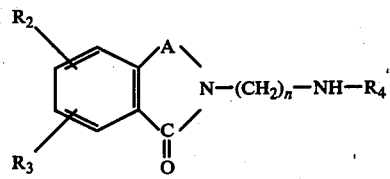

wherein $R_2$, $R_3$, $R_4$, A and n have the same meanings as in formula I, with a phenylalkyl compound of the formula

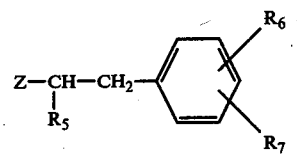

wherein $R_5$, $R_6$ and $R_7$ have the same meanings as in formula I, and
Z has the same meanings as in formula II.

The reaction is carried out in an inert solvent, such as acetone, methylene chloride, dimethylformamide, dimethylsulfoxide or chlorobenzene, and, depending upon the reactivity of substituent Z, at a temperature between 0 and 150° C, but preferably at the boiling point of the particular solvent which is used. The presence of an acid-binding agent, such as an alkali metal alcoholate, an alkali metal hydroxide, an alkali metal carbonate, especially potassium carbonate, or a tertiary organic base, particularly triethylamine or pyridine, or of a reaction accelerator, such as potassium iodide, is of advantage.

Method E

For the preparation of a quinazolinone derivative of the formula I, by reacting a benzoxazin-4-one of the formula

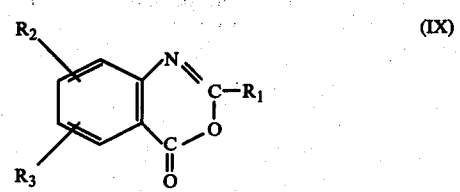

wherein $R_1$, $R_2$ and $R_3$ have the same meanings as in formula I, with an alkylenediamine of the formula

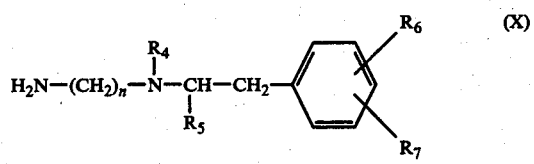

wherein $R_4$, $R_5$, $R_6$ and $R_7$ have the same meanings as in formula I.

The reaction is advantageously carried out in a solvent, such as benzene, dioxane, a lower alkanoic acid such as glacial acetic acid, or dimethylformamide, and optionally in the presence of an acid catalyst at a temperature between 50 and 150° C, but preferably at the boiling point of the particular solvent which is used. The preferred solvent is glacial acetic acid. The reaction may, however, also be performed without a solvent.

If the end product of methods A through E is a compound of the formula I wherein $R_4$ is benzyl, the same may be de-benzylated to yield the corresponding compound wherein $R_4$ is hydrogen. The de-benzylation is preferably effected by means of catalytic hydrogenation, for example with hydrogen in the presence of a catalyst such as palladized charcoal, in a solvent such as ethanol or ethylacetate, at a temperature between 25 and 75° C and at a hydrogen pressure of 1 to 7 atmospheres.

On the other hand, if the end product of methods A through E is a compound of the formula I wherein $R_4$ is hydrogen; the same may be alkylated at the bridge nitrogen atom to form the corresponding compound where $R_4$ is alkyl. The alkylation is carried out with a conventional alkylating agent, for example with an alkyl halide such as methyl iodide, ethyl iodide or isopropyl bromide, or with a dialkylsulfate such a dimethylsulfate, in a solvent such as acetone, dimethylformamide or dioxane, optionally in the presence of an inorganic or tertiary organic base, at a temperature between 0 and 50° C. A methylation may also be effected by reaction with a mixture of formaldehyde and formic acid, preferably at the boiling point of said mixture.

The compounds embraced by formula I are organic bases and therefore form acid addition salts with inorganic or organic acids. Examples of non-toxic, pharmacologically acceptable acid addition salts are those formed with hydrochloric acid, phosphoric acid, hydrobromic acid, sulfuric acid, lactic acid, tartaric acid, maleic acid, 8-chlorotheophylline or the like.

The starting compounds of the formulas II through X are either described in the literature or may be prepared by known methods, as described in the examples below.

The following examples illustrate the present invention and will enable others skilled in the art to understand it more completely. It should be understood, however, that the invention is not limited solely to the particular examples given below.

EXAMPLE 1

1-[4-Methyl-6,7-dimethoxy-1(2H)-phthalazinone-2-yl]-2-[N-methyl-N-(2-(3,4-dimethoxy-phenyl)-ethyl)-amino]-ethane hydrochloride by method A.

(a) 1.2 gm of sodium hydride (50% dispersion in oil) were added to a solution of 5.0 gm (22.7 millimols) of 4-methyl-6,7-dimethoxy-1(2H)-phthalazinone in 50 ml of dimethylformamide. After heating the mixture at 80° C for 20 minutes, the sodium salt of 4-methyl-6,7-dimethoxy-1(2H)-phthalazinone thus obtained was alkylated by the addition of 30 ml of 1,2-dibromo-ethane at 80° C. After 2 hours, the reaction had gone to completion, the precipitated sodium bromide was suction-filtered off and the filtrate was evaporated in vacuo to dryness. The residue was dissolved in chloroform and the chloroform phase was extracted with water, dried over sodium sulphate and evaporated, yielding 5.2 gm (70% of theory) of 1-[4-methyl-6,7-dimethoxy-1(2H)-phthalazinone-2-yl]-2-bromo-ethane, $R_f$-value (chloroform/methanol = 9/1) : 0.8.

(b) A solution of 2.5 gm (7.6 millimols) of 1-[4-methyl-6,7-dimethoxy-1(2H)-phthalazinone-2-yl]-2-bromo-ethane in 50 ml of chlorobenzene was admixed with 1.5 gm (7.6 millimols) of 3,4-dimethoxyphenylethyl-N-methylamine and 3.0 gm of sodium carbonate, and the mixture was refluxed for 20 hours. After cooling, the precipitated solid was filtered off, and the filtrate was evaporated. The residue was chromatographed on silica gel (chloroform/methanol = 100/1), the main fractions were evaporated and the base was precipitated as its hydrochloride, yielding 1.8 gm (49% of theory) of the compound of the formula

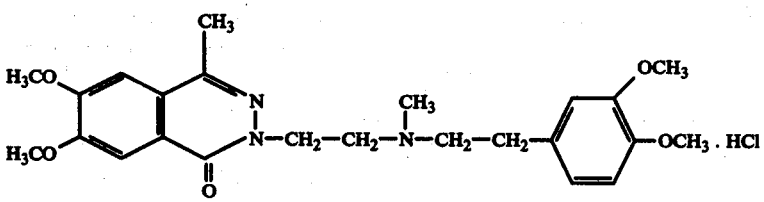

which had a melting point of 204–205° C.

EXAMPLE 2

(a) 1-[4-Methyl-6,7-dimethoxy-1(2H)-phthalazinone-2-yl]-3-chloropropane was prepared analogous to Example 1 (a) by reaction of 4-methyl-6,7-dimethoxy-1(2H)-phthalazinone with 1-bromo-3-chloro-propane in dimethylformamide. $R_f$-value (chloroform/methanol = 9/1) : 0.9.

(b) 1-[4-Methyl-6,7-dimethoxy-1(2H)-phthalazinone-2-yl]-3-[N-methyl-N-(2-(3,4-dimethoxy-phenyl)-ethyl-amino]propane hydrochloride was prepared analogous to Example 1 (b) by reaction of 1-[4-methyl-6,7-dimethoxy-1(2H)-phthalazinone-2-yl]-3-chloro-propane with N-(3,4-dimethoxy-phenylethyl)-N-methyl-amine in chlorobenzene. M.p.: 110 – 115° C. $R_f$-value (chloroform/methanol = 9/1) : 0.45.

EXAMPLE 3

(a) 1-[4-Isopropyl-6,7-dimethoxy-1(2H)-phthalazinone-2-yl]-3-chloro-propane was prepared analogous to Example 1 (a) by reaction of 4-isopropyl-6,7-dimethoxy-1(2H)-phthalazinone with 1-bromo-3-chloro-propane in dimethylformamide. $R_f$-value (chloroform/methanol = 50/1) : 0.5.

(b) 1-[4-Isopropyl-6,7-dimethoxy-1(2H)-phthalazinone-2-yl]-3-[N-methyl-N-(2-(3,4-dimethoxy-phenyl)-ethyl)amino]-propane hydrochloride was prepared analogous to Example 1(b) by reaction of 1-[4-isopropyl-6,7-dimethoxy-1 (2H)-phthalazinone-2-yl]-3-chloro-propane with 3,4-dimethoxyphenylethyl-N-methyl-amine in chlorobenzene. M.p.: 179 – 180° C.

EXAMPLE 4

1-[4-Methyl-6,7-dimethoxy-1(2H)-phthalazinone-2-yl]-3-[N-methyl-N-(2-(4-methoxy-phenyl)-ethyl)-amino]-propane hydrochloride Produced analogously to Example 2 (b) by reaction of 1-[4-methyl-6,7-dimethoxy-1-(2H)-phthalazinone-2-yl]-3-chloro-propane with N-(4-methoxy-phenylethyl)-N-methyl-amine in chlorobenzene. M. p.: 210 – 212° C.

EXAMPLE 5

(a) 1-[6,7-Dimethoxy-1(2H)-phthalazinone-2-yl]-3-chloro-propane was prepared analogous to Example 1 (a) by reaction of 6,7-dimethoxy-1(2H)-phthalazinone with 1-bromo-3-chloro-propane in dimethylformamide. $R_f$-value (chloroform/methanol = 9/1) : 0.9.

(b) 1-[6,7-Dimethoxy-1(2H)-phthalazinone-2-yl]-3-[N-methyl-N-(2-(3,4-dimethoxy-phenyl)-ethyl)-amino]-propane hydrochloride was prepared analogous to Example 1 (b) by reaction of 1-[6,7-dimethoxy-1(2H)-phthalazinone-2-yl]-3-chloro-propane with N-(3,4-dimethoxy-phenylethyl)-N-methylamine in chlorobenzene. M.p.: 200° C.

EXAMPLE 6

(a) 1-[4-Methyl-6,7-dimethoxy-1(2H)-phthalazinone-2-yl]-3-[N-benzyl-N-(2-(3,4-dimethoxy-phenyl)-ethyl)-amino]propane was prepared analogous to Example 1 (a) by reaction of 1-[4-methyl-6,7-dimethoxy-1(2H)-phthalazinone-2-yl]-3-chloro-propane with N-(3,4-dimethoxy-phenylethyl)-N-benzylamine in chlorobenzene. $R_f$-value (chloroform/methanol = 9/1) : 0.9.

(b) 1-[4-Methyl-6,7-dimethoxy-1(2H)-phthalazinone-2-yl]-3-[N-(2-(3,4-dimethoxy-phenyl)-ethyl)-amino]-propane A solution of 2.6 gm (4.4 millmols) of 1-[4-methyl-6,7-dimethoxy-1(2H)-phthalazinone-2-yl]-3-[N-benzyl-N-(2-(3,4-dimethoxy-phenyl)-ethyl)-amino]-amino-propane in 100 ml of ethanol was admixed with 0.3 gm palladium-on-charcoal (10%), and hydrogen was introduced at a temperature of 50° C and 5 atmospheres for 4 hours. After the absorption of hydrogen had ceased the catalyst was filtered off, and the filtrate was evaporated in vacuo leaving the desired free base as a yellow oil. Yield: 1.8 gm (82% of theory). $R_f$-value (chloroform/methanol = 9/1) : 0.4.

EXAMPLE 7

(a) 1-[4-Methyl-6,7-ethylenedioxy-1(2H)-phthalazinone-2-yl]-3-chloro-propane was prepared analogous to Example 1 (a) by reaction of 4-methyl-6,7-ethylenedioxy-1(2H)-phthalazinone with 1-bromo-3-chloro-propane in dimethylformamide. $R_f$-value (chloroform/methanol = 19/1) : 0.9.

(b) 1-4-Methyl-6,7-ethylenedioxy-1(2H)-phthalazinone-2-yl]-3-[N-methyl-N-(2-(3,4-dimethoxy-phenyl)-ethyl)-amino]-propane was prepared analogous to Example 1 (b) by reaction of 1-[4-methyl-6,7-ethylenedioxy-1(2H)-phthalazinone-2-yl]-3-chloro-propane with N-(3,4-dimethoxy-phenylethyl)-N-methyl-amine in chlorobenzene. Yellow oil. $R_f$-value (chloroform/methanol = 9/1) : 0.7.

EXAMPLE 8

1-[4-Methyl-6,7-dimethoxy-1(2H)-phthalazinone-2-yl]-3-[N-methyl-N-(2-(3,4-methylenedioxy-phenyl)-ethyl)-amino]-propane was prepared analogous to Example 2 (b) by reaction of
1-[4-methyl-6,7-dimethoxy-1(2H)-phthalazinone-2-yl]-3-chloropropane with
N-(3,4-methylenedioxy-phenylethyl)-N-methyl amine in chlorobenzene. Yellow oil. $R_f$-value (chloroform/methanol = 9/1) : 0.45.

EXAMPLE 9

1-[4-Methyl-6,7-dimethoxy-1-(2H)-phthalazinone-2-yl]-3-[N-methyl-N-(2-(3,4-dimethoxy-phenyl)-ethyl)-amino]-propane hydrochloride 5.0 gm (11.3 millimols) of the end product of Example 6 (b) were heated in a mixture of 1.38 gm (30 millimols) of formic acid and 1.5 gm (20 millimols) of formalin for 1 hours at 100° C. After cooling, the reaction solution was made alkaline by addition of 2N sodium hydroxide and was then extracted with chloroform. The chloroform phase was washed with water, dried and evaporated in vacuo, and the residue was chromatographed on silica gel (chloroform/methanol = 100/1). The main fractions were evaporated, and the base was precipitated as its hydrochloride from ethereal hydrochloric acid. M.p.: 110–115° C.

EXAMPLE 10

1-[4-Methyl-6,7-dimethoxy-1-(2H)-phthalazinone-2-yl]-3-[N-(2-(3,4-dimethoxy-phenyl)-ethyl)-amino]-propane by method C A solution of 3.0 gm (11.3 millimols) of 3-(4-methyl(6,7-dimethoxy-1(2H)-phthalazinone-2-yl)-propionaldehyde and 2.0 gm (11.3 millimols) of 3,4-dimethoxy-phenylethylamine in 100 ml of ethanol was admixed with 0.3 gm of palladium-on-charcoal (10%), and hydrogen was introduced at a temperature of 50° C and 5 atmospheres for 4 hours. After the absorption of hydrogen had ceased, the catalyst was filtered off. The filtrate was evaporated in vacuo, leaving the desired base as a viscous yellow oil. Yield: 3.7 gm (67% of theory). $R_f$-value (chloroform/methanol = 9/1) : 0.4.

EXAMPLE 11

(a) 1-(6,7-Dimethoxy-4(3H)-quinazolinone-3-yl)-2-bromo-ethane was prepared analogous to Example 1 (a) by reaction of 6,7-dimethoxy-4(3H)-quinazolinone with 1,2-dibromoethane in dimethylformamide. Viscous oil. $R_f$-value (chloroform/methanol = 9/1) : 0.85.

(b) 1-(6,7-dimethoxy-4(3H)-quinazolinone-3-yl)-2-[N-methyl-N-(2-(3,4-dimethoxy-phenyl)-ethyl)-amino]-ethane hydrochloride was prepared analogous to Example 1 (b) by reaction of 1-(6,7-dimethoxy-4(3H)-quinazolinone-3-yl)-2-bromoethane with N-(3,4-dimethoxy-phenyl ethyl)-N-methyl amine in chlorobenzene. M.p.: 205 - 208° C.

EXAMPLE 12

(a) 1-(6,7-Dimethoxy-4-(3H)-quinazolinone-3-yl)-3-chloro-propane was prepared analogous to Example 1 (a) by reaction of 6,7-dimethoxy-4(3H)-quinazolinone with 1-bromo-3-chloro-propane in dimethyl-formamide. $R_f$-value (chloroform/methanol = 19/1) : 0.75.

(b) 1-(6,71 -Dimethoxy-4(3H)-quinazoline-3-yl)3-[N-methyl-N-(2-(3,4-dimethoxy-phenyl)-ethyl)-amino]-propane-hydrochloride was prepared analogous to Example 1 (b) by reaction of 1-(6,7-dimethoxy-4(3H)-quinazoline-3-yl)-3-chloro-propane with N-(3,4-dimethoxy-phenyl ethyl)-N-methylamine in chlorobenzene. $R_f$-value (chloroform/methanol = 9/1) : 0.4.

EXAMPLE 13

(a) 1-(6,7-Dimethoxy-4(3H)-quinazolinone-3-yl)-3-[N-benzyl-N-(2-(3,4-dimethoxy-phenyl)-ethyl)-amino]-propane was prepared analogous to Example 1 (a) by reaction of 1-(6,7-dimethoxy-4(3H)-quinazolinone-3-yl)-3-chloro-propane with N-(3,4-dimethoxy-phenylethyl)-N-benzyl amine in chlorobenzene. $R_f$-value (chloroform/methanol = 9.1) : 0.75.

(b) 1-(6,7-Dimethoxy-4(3H)-quinazolinone-3-yl)-3-[N-(2-(3,4-dimethoxy-phenyl)-ethyl)-amino]-propane-hydrochloride was prepared analogous to Example 6 (b) by debenzylation of 1-(6,7-dimethoxy-4-(3-H)-quinazolinone-3-yl)-3-[N-benzyl-(2-(3,4-dimethoxy-phenyl)-ethyl)-amino]-propane in the presence of palladium-on-charcoal (10%) with hydrogen. $R_f$-value (chloroform/methanol = 9.1) : 0.45. M.p.: 192 –194° C.

EXAMPLE 14

1-(2-Methyl-6,7-dimethoxy-4(3H)-quinazolinone-3-yl)-3-[N-methyl-N-(2(3,4-dimethoxy-phenyl)-ethyl)-amino]-propane hydrochloride by method E A solution of 3.0 gm (13.5 millimols) of 1-[N-methyl-N-(2(3,4-dimethoxy-phenyl)-ethyl)-amino]-3-aminopropane and 3.3 gm (13.0 millimols) of 2-methyl-4H-3,1-benzoxazine-4-one in 50 ml of glacial acetic acid was refluxed for 4 hours. Then, the mixture was evaporated in vacuo, the residue was digested in 2N sodium hydroxide, and the alkaline aqueous mixture was extracted with chloroform. The chloroform phase was washed with a saturated aqueous sodium carbonate solution and with water, dried over sodium sulfate and evaporated. The raw product was purified by means of chromatography (chloroform/methanol = 30/1) on silica gel. By addition of ethereal hydrochloric acid to a solution of the purified product in acetone, the hydrochloride was precipitated and recrystallized from acetone/methanol. Yield: 3.9 gm (61% of theory) of the compound of the formula

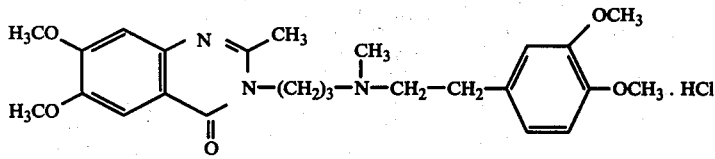

having a melting point of 215 – 217° C.

EXAMPLE 15

1-(2-Methyl-6,7-dimethoxy-4(3H)-quinazolinone-3-yl)-3-[N-(2-(3,4-dimethoxy-phenyl)-ethyl)-amino]-propane hydrochloride was prepared analogous to Example 14 by reaction of 2-methyl-4H-3,1-benzoxazine-4-one with 1-[N-(2-(3,4-dimethoxy-phenyl)-ethyl)-amino]-3-amino-propane in glacial acetic acid. M.p.: 243 – 245° C.

EXAMPLE 16

(a) 1-(2-Methyl-6,7-dimethoxy-4(3H)-quinazolinone-3-yl)-2-methylamino-ethane was prepared analogous to Example 14 from N-methyl-ethylene-diamine and 2-methyl-4H-3,1-benzoxazine-4one in glacial acetic acid. Viscous oil. Yield: 53% of theory.

(b) 1-(2-Methyl-6,7-dimethoxy-4(3H)- quinazolinone-3-yl)-2-[N-methyl-N-(2-(3,4-dimethoxy-phenyl)-ethyl)-amino]-ethane hydrochloride by method D.

A mixture of 2.0 gm (7.2 millimols) of 1-(2-methyl-4,7-dimethoxy-4(3H)-quinazolinone-3-yl)-2-methylaminoethane, 1.4 gm (7.0 millimols) of 3,4-dimethoxy-phenylethyl chloride, 3.0 gm of potassium carbonate and a small quantity of potassium jodide was refluxed in chlorobenzene for 48 hours. After cooling, the solution was filtered, and the filtrate was evaporated in vacuo to dryness. The raw product was purified by chromatography on silica gel (chloroform/methanol = 50/1). The evaporation residue of the main fraction was dissolved in acetone, and the hydrochloride was precipitated by addition of ethereal hydrochloric acid. Yield: 1.1 gm (30% of theory). M.p.: 237 – 239° C.

EXAMPLE 17

1-[4-Methyl-6,7-dimethoxy-1(2H)-phthalazinone-2-yl]-3-[N-methyl-N-(2-(3,4-dimethoxy-phenyl)-ethyl)-amino]-propane hydrochloride by method B 0.5 gm of sodium hydride were added to a solution of 3.0 gm (13.0 millimols) of 4-methyl-6,7-dimethoxy-1(2H)-phthalazinone in 100 ml dimethylformamide. After heating the mixture at 80° for 30 minutes, a solution of 8.5 gm (35.2 millimols) of 1-[N-methyl-N-(2-(3,4-dimethoxy-phenyl)-ethyl)-amino]-3-bromo-propane in 100 ml of dimethylformamide was added dropwise. After heating the resulting mixture at 140° C for 8 hours, the reaction mixture was cooled, diluted with water and extracted several times with chloroform. The organic phase was dried over sodium sulfate and evaporated to dryness in vacuo. The residue was chromatographed (chloroform/methanol = 100/1) on silica gel. Then, the evaporation residue of the main fraction was dissolved in acetone, and the base was precipitated as its hydrochloride. Yield: 0.6 gm (10% of theory). M.p.: 110 – 115° C.

The compounds of the present invention, that is, those embraced by formula I and their non-toxic, pharmacologically acceptable acid addition salts, have useful pharmacodynamic properties. More particularly, they exhibit heart rate lowering and mild antihypertensive activities in warm-blooded animals, such as cats and dogs.

The effect of the compounds of this invention upon the heart rate was ascertained by the test method described below, and the results for a few representative species are shown in the tables, where A = 1-[4-Methyl-6,7-dimethoxy-1(2H)-phthalazinone-2-yl]-3-[N-methyl-N-(2-(3,4-dimethoxyphenyl)-ethyl)-amino]-propane hydrochloride, B = 1-[4-Methyl-6,7-dimethoxy-1(2H)-phthalazinone-2-yl]-3-[N-methyl-N-(2-(4-methoxyphenyl)-ethyl)-amino]-propane hydrochloride, C = 1-[4-Isopropyl-6,7-dimethoxy-1(2H)-phthalizinone-2-yl]-3-[N-methyl-N-(2-(3,4-dimethoxy-phenyl)-ethyl)-amino]-propane hydrochloride, D = 1-[6,7-Dimethoxy-1(2H)-phthalazinone-2-yl]-3-[N-methyl-N-(2-(4-methoxyphenyl)-ethyl)-amino]-propane hydrochloride, and E = 1-[4-Methyl-6,7-dimethoxy-1(2H)-phthalizinone-2-yl]-3-[N-methyl-N-(2-(3,4-dimethoxyphenyl)-ethyl)-amino]-ethane hydrochloride.

The effect of the test compound on the heart rate was tested at various dosage levels on 2 – 5 cats or dogs of both sexes per dose. The average body weight of the cats was 2.5 – 3.5 kg, and that of the dogs was 18 – 28 kg. For this purpose the animals were anesthetized with nembutal (30 mg/kg i.p.) and chloralose-urethane (40 mg/ml chloralose + 200 mg/ml urethane as required). The test compound in aqueous solution was injected into the Vena saphena (i.v.) or duodenum (i.p.).

The heart rate was registered before and after administration of the test compound on a Grass-polygraph by means of a Grass-tachograph from the electrocardiogram (precordial lead). The following tables show the results obtained.

Table I

| | Tests on cats | | |
|---|---|---|---|
| Compound | Dosage mg/kg | Decrease in heart rate beats/minute | Duration of Effective action in minutes |
| A | 0.5 i.v. | −16 | >50 |
| A | 1.0 i.v. | −23 | >70 |
| A | 2.0 i.v. | −37 | >70 |
| A | 2.0 i.d. | −25 | >74 |
| A | 4.0 i.d. | −34 | >60 |
| A | 10.0 i.d. | −41 | >>50 |
| D | 0.5 i.v. | −6 | 10 |
| D | 1.0 i.v. | −13 | 25 |
| D | 2.0 i.v. | −14 | 25 |
| E | 1.0 i.v. | −10 | 9 |
| E | 2.0 i.v. | −13 | 10 |

Table II

| | Tests on dogs | | |
|---|---|---|---|
| Compound | Dosage mg/kg | Decrease in heart rate beats/minute | Duration of Effective action in minutes |
| A | 0.25 i.v. | −10 | 17 |
| A | 0.5 i.v. | −12 | 15 |
| A | 1.0 i.v. | −16 | 24 |
| B | 0.25 i.v. | −6 | 24 |

Table II-continued

Tests on dogs

| Compound | Dosage mg/kg | Decrease in heart rate beats/minute | Duration of Effective action in minutes |
|---|---|---|---|
| B | 1.0 i.v. | −23 | 46 |
| C | 1.0 i.v. | −10 | 17 |
| C | 2.0 i.v. | −29 | 10 |

Additionally, it should be noted that at all dosage levels the test compounds were tolerated very well and produced no toxic side-effects. The $LD_{50}$ for compound A in mice, for example, was determined to be 63 mgm/kg i.v. with an observation time of 14 days.

Thus, the compounds of this invention are useful for the treatment of pectanginal disorders, especially for the treatment of chronic coronary insufficiency.

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.83 to 4.17 mgm/kg body weight.

The following examples illustrated a few pharmaceutical dosage unit compositions comprising a compound of the present invention as an active ingredient and represent the best modes contemplated of putting the invention into practical use. The parts are parts by weight unless otherwise specified.

EXAMPLE 18

Tablets

The tablet composition is compounded from the following ingredients:

| | | |
|---|---|---|
| 1-[4-Methyl-6,7-dimethoxy-1(2H)-phthalazinone-2-yl]-3-[N-methyl-N-(2-(3,4-dimethoxy-phenyl)-ethyl)-amino]-propane hydrochloride | 100.0 | parts |
| Lactose | 50.0 | parts |
| Polyvinylpyrrolidone | 5.0 | parts |
| Carboxymethyl cellulose | 19.0 | parts |
| Magnesium stearate | 1.0 | parts |
| Total | 175.0 | parts |

Preparation

The active ingredient and the lactose are intimately admixed with each other, the mixture is uniformly moistened with an aqueous solution of the polyvinylpyrrolidone, and the moist mass is granulated by passing it through a finemesh screen. The granulate is then dried and admixed with the remaining ingredients, and the composition is compressed into 175 mgm-tablets in a conventional tablet making machine. Each tablet contains 100 mgm of the active ingredient and is an oral dosage unit composition.

EXAMPLE 19

Coated pills

The pill core composition is compounded from the following ingredients:

| | | |
|---|---|---|
| 1-[4-Methyl-6,7-dimethoxy-1(2H)-phthalazinone-2-yl]-3-[N-methyl-N-(2-(3,4-dimethoxy-phenyl)-ethyl)-amino]-propane hydrochloride | 50.0 | parts |
| Corn starch, dry | 20.0 | parts |
| Soluble starch | 2.0 | parts |
| Carboxymethyl cellulose | 7.0 | parts |
| Magnesium stearate | 1.0 | parts |
| Total | 80.0 | parts |

Preparation

The ingredients are compounded in analogy to the preceding example, and the composition is compressed into 80 mgm-pill cores which are subsequently coated with a thin shell consisting essentially of a mixture of sugar and gumarabic. Each coated pill contains 50 mgm of the active ingredient and is an oral dosage unit composition.

EXAMPLE 20

Suppositories

The suppository composition is compounded from the following ingredients:

| | | |
|---|---|---|
| 1-[4-Methyl-6,7-dimethoxy-1(2H)-phthalazinone-2-yl]-3-[N-methyl-N-(2-(3,4-dimethoxy-phenyl)-ethyl)-amino]-propane hydrochloride | 150.0 | parts |
| Supossitory base (e.g. cocoa butter) | 1550.0 | parts |
| Total | 1700.0 | parts |

Preparation

The active ingredient is uniformly blended into the molten suppository base, and 1.7 gm-portions of the liquid mixture are poured into cooled suppository molds and allowed to harden therein. Each suppository is a rectal dosage unit composition containing 150 mgm of the active ingredient.

EXAMPLE 21

Suspension

The suspension is compounded from the following ingredients:

| | | |
|---|---|---|
| 1-[4-Methyl-6,7-dimethoxy-1(2H)-phthalazinone-2-yl]-3-[N-methyl-N-(2-(3,4-dimethoxy-phenyl)-ethyl)-amino]-propane hydrochloride | 5.0 | parts |
| Carboxymethyl cellulose | 0.1 | parts |
| Methyl p-hydroxybenzoate | 0.05 | parts |
| Propyl p-hydroxybenzoate | 0.01 | parts |
| Sugar | 10.0 | parts |
| Glycerin | 5.0 | parts |
| Sorbitol solution 70% | 20.0 | parts |
| Flavoring | 0.3 | parts |
| Distilled water q.s.ad | 100.0 by vol. | parts |

Preparation

While stirring, the p-hydroxybenzoates, the glycerin and the carboxymethyl cellulose are dissolved in the distilled water at 70° C. The resulting solution is cooled to room temperature and, while stirring, the active ingredient is added and homogeneously dispersed therein. Thereafter, the sugar, the sorbitol solution and the flavoring are added and dissolved in the dispersion, and the composition is deaerated by stirring in vacuo. The suspension is an oral dosage unit composition, 5 ml of which contain 250 mgm of the active ingredient.

Any one of the other compounds embraced by formula I or a non-toxic, pharmacologically acceptable acid addition salt thereof may be substituted for the particular active ingredient in Examples 18 through 21. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

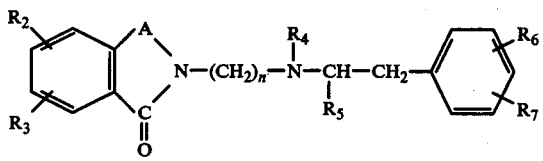

wherein A is

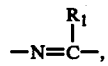

where $R_1$ is hydrogen or alkyl of 1 to 3 carbon atoms;
$R_2$ is alkoxy of 1 to 3 carbon atoms;
$R_3$ is alkoxy of 1 to 3 carbon atoms or, together with $R_2$, methylenedioxy or ethylenedioxy;
$R_4$ is hydrogen, alkyl of 1 to 3 carbon atoms or benzyl;
$R_5$ is hydrogen or alkyl of 1 to 3 carbon atoms;
$R_6$ is hydrogen or alkoxy of 1 to 3 carbon atoms;
$R_7$ is alkoxy of 1 to 3 carbon atoms or, together with $R_6$, methylenedioxy or ethylenedioxy; and
n is 2 or 3;
or a non-toxic, pharmacologically acceptable acid addition salt thereof.

2. A compound of claim 1,
where A is

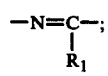

$R_1$ and $R_5$ are each hydrogen, methyl, ethyl, n-propyl or isopropyl;
$R_4$ is hydrogen, methyl, ethyl, n-propyl, isopropyl or benzyl;
$R_2$, $R_3$ and $R_7$ are each methoxy, ethoxy, n-propoxy or isopropoxy;
$R_6$ is hydrogen, methoxy, ethoxy, n-propoxy or isopropoxy;

$R_2$ and $R_3$, together with each other, are methylenedioxy or ethylenedioxy;
$R_6$ and $R_7$, together with each other, are methylenedioxy or ethylenedioxy; and
n is 2 or 3;
or a non-toxic, pharmacologically acceptable acid addition salt thereof.

3. A compound of claim 1,
where A is

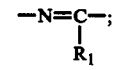

$R_1$ is hydrogen, methyl or isopropyl;
$R_2$ is methoxy;
$R_3$ is methoxy or, together with $R_2$, methylenedioxy or ethylenedioxy;
$R_4$ is hydrogen, methyl or benzyl;
$R_5$ is hydrogen;
$R_6$ is hydrogen or methoxy;
$R_7$ is methoxy or, together with $R_6$, methylenedioxy or ethylenedioxy; and
n is 2 or 3;
or a non-toxic, pharmacologically acceptable acid addition salt thereof.

4. A compound of claim 1,
where A is

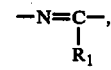

where $R_1$ is hydrogen or methyl;
$R_2$ and $R_3$, are methoxy in the 6- and 7-position, respectively, or, together with each other, 6,7-methylenedioxy or 6,7-ethylenedioxy;
$R_4$ is hydrogen or methyl;
$R_5$ is hydrogen;
$R_6$ is hydrogen or methoxy in the 3-position;
$R_7$ is methoxy in the 4-position or, together with $R_6$, 3,4-methylenedioxy or 3,4-ethylenedioxy; and
n is 2 or 3;
or a non-toxic, pharmacologically acceptable acid addition salt thereof.

5. A compound of claim 4, which is 1-[4-methyl-6,7-dimethoxy-1(2H)-phthalazinon-2-yl]-3-[N-methyl-N-(2-(3,4-dimethoxy-phenyl)-ethyl)-amino]-propane or a non-toxic, pharmacologically acceptable acid addition salt thereof.

6. A pharmaceutical dosage unit composition consisting essentially of an inert pharmaceutical carrier and an effective heart rate reducing amount of a compound of claim 1.

7. The method of reducing the heart rate in a warm-blooded animal in need thereof, which comprises per-orally, parenterally or rectally administering to said animal an effective amount of a compound of claim 1.

* * * * *